United States Patent [19]

Burrows et al.

[11] Patent Number: 5,497,102

[45] Date of Patent: Mar. 5, 1996

[54] METHOD AND APPARATUS FOR DETECTION OF LIQUID INCENDIARIES BY CHANGES IN CAPACITANCE

[75] Inventors: John D. Burrows; Kenneth R. Mann, both of Farnborough, United Kingdom

[73] Assignee: Her Majesty the Queen in right of Canada, as represented by the Secretary of State for Defence in Her Britannic Majesty's Government of the United Kingdom of Great Britain and Northern Ireland, Canada

[21] Appl. No.: 295,018

[22] Filed: Aug. 24, 1994

[30] Foreign Application Priority Data

Aug. 25, 1993 [GB] United Kingdom ................... 9317633

[51] Int. Cl.$^6$ .......................... G01R 27/26; G01N 27/22
[52] U.S. Cl. ........................ 324/663; 324/686; 324/690; 73/61.41
[58] Field of Search ..................................... 324/658, 659, 324/663, 664, 665, 671, 672, 679, 686, 689, 690; 73/61.41, 61.43, 61.44

[56] References Cited

U.S. PATENT DOCUMENTS

| | | | |
|---|---|---|---|
| 2,285,152 | 6/1942 | Firestone | 324/671 |
| 2,724,798 | 11/1955 | Hare et al. | 324/663 |
| 3,708,064 | 1/1973 | Schepler et al. | 324/671 X |
| 4,710,757 | 12/1987 | Haase | 324/663 X |
| 5,135,485 | 8/1992 | Cohen et al. | 324/606 X |

FOREIGN PATENT DOCUMENTS

| | | | |
|---|---|---|---|
| 0193343 | 11/1984 | Japan | 324/690 |
| 5072349 | 3/1993 | Japan | 324/663 |

Primary Examiner—Kenneth A. Wieder
Assistant Examiner—Diep Do
Attorney, Agent, or Firm—Nixon & Vanderhye

[57] ABSTRACT

A device fop detecting liquid incendiaries contained in bottles comprises a flexible cradle, such as a sling of thin rubber sheet (2), mounted between two supports (4); two conductors arranged laterally on the cradle (6), each conductor having a large surface area to thickness ratio; and an electrical circuit including a power source and indication means to provide an indication of the dielectric properties of a bottle placed within the cradle.

15 Claims, 2 Drawing Sheets

METHOD AND APPARATUS FOR DETECTION OF LIQUID INCENDIARIES BY CHANGES IN CAPACITANCE

BACKGROUND OF THE INVENTION

1. Field of the Invention

The invention relates to the screening of bottles and similar containers to detect liquid incendiaries contained therein.

2. Discussion of the Prior Art

Liquid incendiaries such as petrol, turpentine and methylated spirits pose a considerable threat to aviation security. Such liquids can be readily transported onto aircraft contained within commonplace bottles such as are normally used to contain water-based or alcoholic beverages. In order to minimize this potential risk it is desirable that security procedures at airports include a quick and reliable method of screening bottles for incendiary liquids.

Visual inspection of bottles to look for signs of tampering with the seal is no longer a reliable technique. The increased availability of home brewing kits provides a capacity for a professional seal to be made on a bottle, thus rendering apparently innocuous a bottle which has been tampered with. However, it is impractical for airport security staff to open every bottle in order to determine the contents. A suitable screening procedure should therefore be able to distinguish between beverages and common incendiary liquids whilst the bottle remains sealed.

SUMMARY OF THE INVENTION

The present invention utilizes the differences in dielectric properties of common liquids to provide a means of detecting a number of common incendiary liquids. The dielectric constant of water is around 80 at room temperature. The addition of alcohol produces a mixture with reduced dielectric constant, but for alcohol contents within a typical range for beverages (eg 10% for wines, 40% for spirits) the dielectric constant still lies in the range of approximately 60–70. By contrast, the dielectric constants of many readily available incendiary liquids are below 20. The present invention is therefore directed to the provision of a simple bottle screening device capable of detecting differences in the capacitance of a filled bottle and thereby detecting such differences in the dielectric properties of liquids contained therein.

Thus according to the present invention there is provided a device for detecting liquid incendiaries contained in bottles comprising a flexible cradle mounted between two supports, two conductors arranged laterally on the cradle, each conductor having a large surface area to thickness ratio, an electrical circuit comprising an alternating current power source and indication means responsive to the strength of the signal in the circuit and electrical connection means for connecting the conductors into the circuit, so that in use with a bottle placed within the cradle an indication is provided of the dielectric properties of the bottle.

In use the device approximates to a parallel plate capacitor. Applying a power supply and passing the resultant signal through a detector responsive to variations in the signal arising from variations in dielectric properties between bottles containing different liquids provides a simple method of comparatively screening similar bottles. It is therefore important that the conductors are configured so that they lie approximately parallel and opposite one another when a bottle is inserted. The conductors are thus preferably arranged equidistant from the supports so that in use they lie disposed substantially opposite each other in contact with the surface of a bottle placed in the cradle, that is to say in contact with opposite sides of a square bottle or diametrically opposing points on the surface of a bottle having circular cross-section. It will be evident that the exact configuration of a device for optimum performance will depend on bottle size and shape. In practice however the vast majority of bottles encountered are likely to be of similar size (0.75–1.5 l, circular cross section) so that the device offers a simple way of screening unopened bottles for many common incendiary liquids.

Accurate results require a good contact being maintained between bottle surface and conductors. The cradle is therefore flexible so as to be conformable to the shape of the bottle and is preferably a sling comprising a sheet of flexible material. Most preferably, this is a thin rubber sheet which has a minimum effect on the signal response of the device when a bottle is contained within it.

The electrical circuit preferably further comprises a rectifier to convert the ac signal produced when the power source is applied to the device to a dc signal, with the indication means comprising a dc voltage indicator electrically connected thereto.

It has been noted that the dielectric constant of most alcoholic drinks lies in the range of approximately 60–70, whereas the dielectric constants of many readily available incendiary liquids are below 20. The invention is directed principally at distinguishing between these two ranges and in particular at detecting the signal response of bottles containing liquids having dielectric constants within the critical range corresponding to many incendiaries. It will be apparent therefore that whilst the indication means needs to provided an indication of whether the dielectric constant of a bottle containing liquid lies within this predetermined critical range, it is not necessary that it comprises a means to give an analogue measurement of the signal in the circuit which can be related to an analogue measurement of dielectric constant. The indication means may also conveniently comprise a means to indicate whether or not the signal is in a particular predetermined range. Thus, the voltage indicator may be a variable voltage threshold device which is adapted to be preset to a predetermined threshold voltage level and incorporates signalling means actuatable when the predetermined threshold voltage level is exceeded by the dc signal.

A simple signalling means, which could be in the form of a light emitting diode, an audio alarm configured to sound when the threshold voltage is exceeded, or similar device, allows rapid processing of bottles through the device on a pass/fail basis. Bottles which fail the test can be subjected to further examination.

In use, the predetermined threshold voltage level is preset to a level between that which would be expected in the circuit when a bottle of dielectric constant in the alcoholic drink range (60–70) is placed within the cradle, and that which would be expected in the circuit when a bottle of dielectric constant in the incendiary liquid range (below 20) is placed within the cradle. The preset voltage will depend on circuit characteristics. Provided the bottles under test are not too dissimilar, adequate sensitivity can be achieved by presetting a threshold voltage at the signal response corresponding to a dielectric constant of the order of 35.

The voltage indicator may comprise, either alternatively or additionally to the foregoing, a voltmeter. This allows voltage readings for unusual suspect bottles to be compared with identical bottles of known contents so that more reliable results are obtained, and also enables an appropriate predetermined voltage level to be set by reference to a bottle of known contents.

It has been noted that a particular cradle and conductor configuration will only be suited to a range of bottle sizes. Moreover, a different signal response can result from bottles of different shape, such as those having square or triangular cross section. It is possible therefore to provide a plurality of the above described devices configured and precalibrated appropriately for a plurality of different bottle shapes and size ranges. Such a system allows bottles of non-standard sizes and shapes to be screened. As in practice there is only limited variation between the vast majority of bottles, a comprehensive system can be obtained from a small number of such devices.

The invention also provides for a method of detecting liquid incendiaries contained in bottles comprising the use of a device as described in the foregoing in conjunction with a bottle containing liquid of a suspect composition.

The method comprises arranging two conductors laterally on a Flexible cradle mounted between two supports, each conductor having a large surface area to thickness ratio; connecting the conductors into an electrical circuit comprising an alternating current power source and indication means responsive to the strength of the signal in the circuit; placing a bottle containing liquid within the cradle; activating the power source to apply an alternating current to the circuit; and observing the response of the indication means so as to obtain an indication of the dielectric properties of the bottle. The method thus offers a simple way of screening unopened bottles by monitoring dielectric properties and exploiting the characteristic differences which would be expected in these properties between innocent liquids and many common incendiary liquids.

BRIEF DESCRIPTION OF THE FIGURES

The invention will now be described by way of example only with reference to FIGS. 1 to 4 in which.

DETAILED DISCUSSION OF PREFERRED EMBODIMENTS

Figure 1:
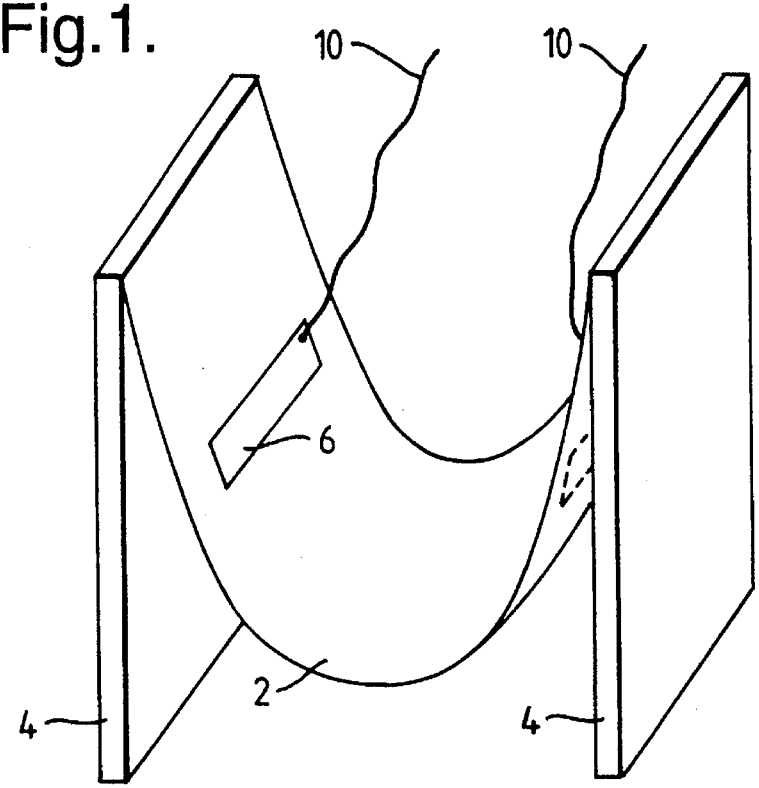
FIG. 1 is a perspective view of the region of the sling in an embodiment of device according to the invention.

FIG. 1 illustrates a sling 2 of thin sheet rubber supported between two parallel supports 4 comprising plastic blocks. The rubber is chosen to be conformable to bottle shape so that the sling is applicable to a range of bottle shapes and sizes and both materials selected are of low dielectric constant so that interference with test measurements is minimized.

A pair of thin copper strips 6 are located on the sling 2 in a parallel configuration to form the contacts, and each is held in place by a plastic strip cover glued over the copper strip 6 and onto the rubber of the sling 2. The use of narrow strip contacts is preferred as it helps to ensure that an intimate contact between bottle and strip is maintained. With wider strips air gaps are more likely and the dielectric properties of the air in such a gap would then affect the result. A conducting wire 10 is electrically connected to each copper strip 6 to provide a means for connecting the arrangement into a circuit.

Figure 2:
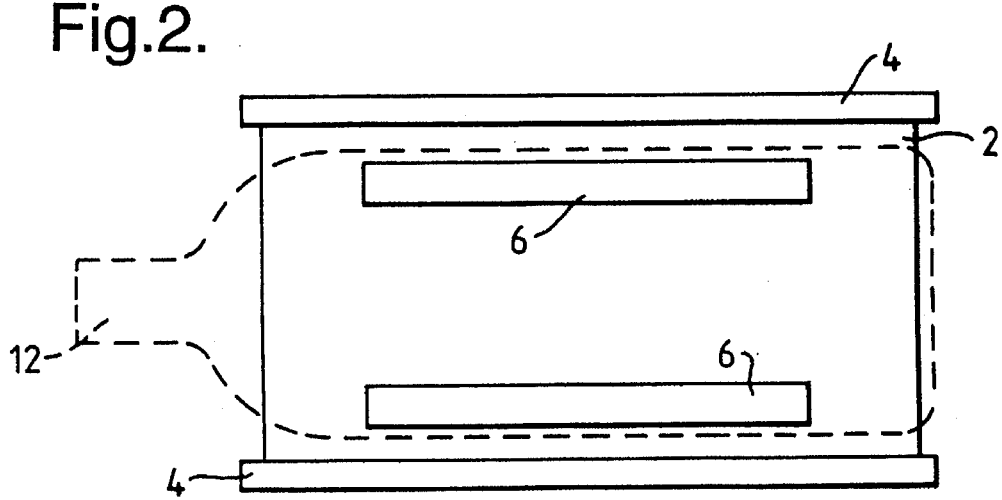
FIG. 2 is a plan view of the sling of FIG. 1 illustrating the positioning of a bottle when the device is in use.

FIG. 2 shows the arrangement of FIG. 1 in plan view with a bottle positioned for testing shown in outline by the broken line 12. A bottle to be tested is positioned with its longitudinal axis parallel to the blocks 4 and supported by the sling 2 so that bottle and contents lie between the copper strips 6 and function as the dielectric medium of a capacitor. The bottle is positioned with the main label uppermost, so that a good contact is achieved between the copper strip contact plates 6 and the glass surface of the bottle.

Figure 3:
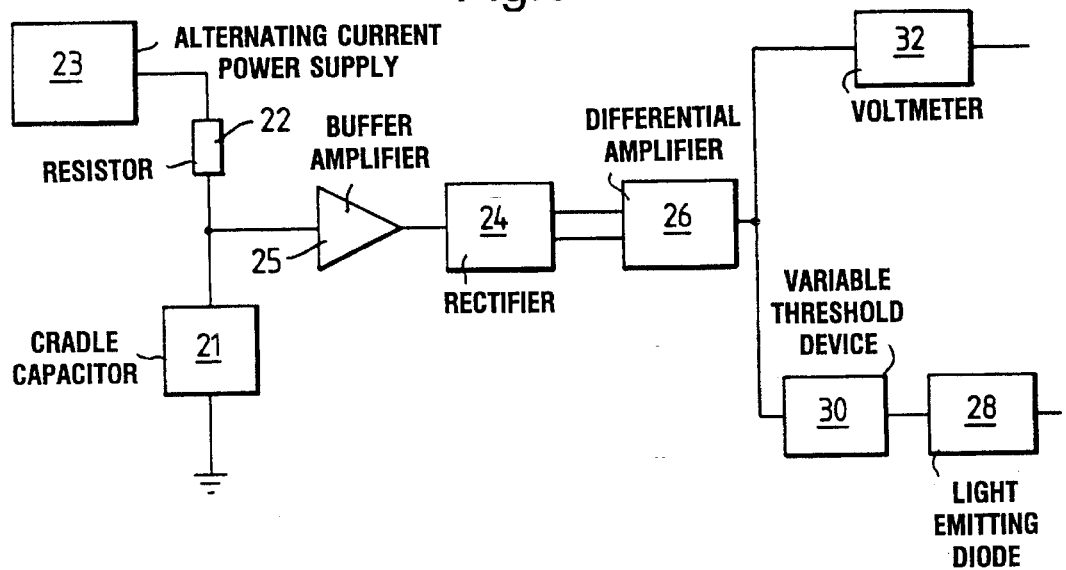
FIG. 3 is a schematic of an arrangement of components including the sling of FIG. 1 into a bottle screening device in accordance with an embodiment of the invention.

A simple schematic of a circuit incorporating the cradle capacitor arrangement of FIGS. 1 and 2 to provide a bottle screening device is shown in FIG. 3. The cradle capacitor 21 and a 220K ohm resistor 22 are connected to an alternating current power supply 23 which applies a 500 Hz square wave signal. The capacitance of the cradle arrangement 21 changes depending on the contents of the bottle placed within it. The lower the capacitance, the larger the output signal which is generated. The signal is then passed to a high input impedance buffer 25. The alternating current output of the buffer 25 is converted to direct current by a rectifier 24 and differential amplifier 26. The dc voltage can be read from a voltmeter 32. It is also used to drive an alarm in the form of a variable threshold voltage device 30 and light emitting diode 28 which combination is adjusted to ensure that the light emitting diode 28 is illuminated when the output signal reaches a particular predetermined threshold voltage. The voltmeter 32 can also be used to set a predetermined voltage level of appropriate sensitivity by reference to a bottle of known contents.

Figure 4:
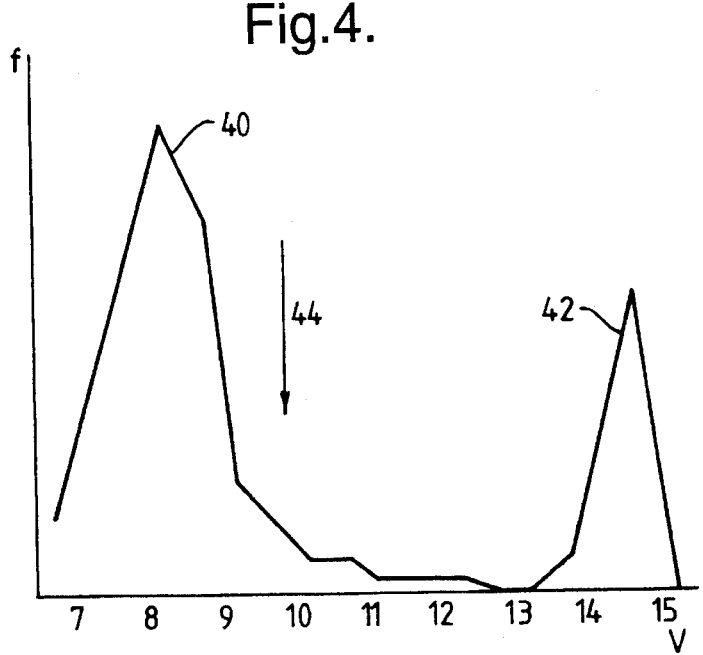
FIG. 4 is a graphical representation of an example set of results produced by the arrangement of FIG. 3 in use with a series of test bottles.

FIG. 4 illustrates a set of readings produced by a series of bottles containing either water or petrol to illustrate the method of calibration. The relative frequency of occurrence (f) of a particular signal voltage is plotted against the voltage (V). Distinct peaks can be seen for water 40 and petrol 42 with very few bottles giving a signal of intermediate voltage. This allows the setting of a threshold voltage 44, in this case of around 10 V, which is done by adjusting the light emitting diode 28 and potentiometer 30 combination of FIG. 3 so that the light emitting diode is illuminated when the signal in the circuit reaches or exceeds the threshold. Once calibrated, the device provides a simple pass/fail test system, in which suspect bottles may be placed in the sling as above described and rapidly checked.

We claim:

1. A device for detecting liquid incendiaries contained in a bottle, said device comprising:

a flexible cradle mounted between two supports, said cradle supporting said bottle, two conductors arranged laterally on the cradle to form a capacitor, an electrical circuit comprising an alternating current power source applied to said conductors whereby a signal is developed with a strength proportional to capacitance of said capacitor, and indication means responsive to the strength of the signal in the circuit.

2. A device according to claim 1 wherein the conductors are arranged equidistant from the supports so that in use they lie disposed substantially opposite each other in contact with the surface of a bottle placed in the cradle.

3. A device according to claim 1 wherein the cradle is in the form of a sling comprising a thin rubber sheet.

4. A device according to claim 1 wherein the electrical circuit further comprises a rectifier to convert the ac signal produced when the power source is applied to the device to a dc signal, and the indication means is a dc voltage indicator electrically connected thereto.

5. A device according to claim 4 wherein the voltage indicator comprises a variable voltage threshold device which is adapted to be preset to a predetermined threshold voltage level and incorporates signalling means actuatable when the predetermined threshold voltage level is exceeded by the dc signal.

6. A device according to claim 4 wherein the voltage monitor comprises a voltmeter.

7. A device according to claim 5 wherein the voltage monitor comprises a voltmeter.

8. A device according to claim 1, wherein said signal is developed with a strength indirectly proportional to the capacitance of said capacitor.

9. A method of detecting a liquid incendiary contained in a bottle comprising the steps of:

arranging two conductors laterally on a flexible cradle mounted between two supports, said conductors forming a capacitor;

connecting the capacitor into an electrical circuit comprising an alternating current power source and indication means responsive to the strength of the signal developed across the capacitor;

placing a bottle containing liquid within the cradle;

activating the power source to apply an alternating current to the circuit; and observing the response of the indication means so as to obtain an indication of capacitance of the capacitor and thus the dielectric properties of the bottle.

10. A method according to claim 9 wherein the conductors are arranged equidistant from the supports so as to be disposed substantially opposite each other in contact with the sides of the bottle.

11. A method according to claim 9 wherein the conductors are arranged on a cradle which is is in the form of a sling comprising a thin rubber sheet.

12. A method according to claim 9 wherein the electrical circuit has incorporated into it a rectifier to convert the ac signal produced when the power source is applied to the device to a dc signal, and indication means comprising a dc voltage indicator electrically connected thereto.

13. A method according to claim 12 wherein the voltage indicator comprises a variable voltage threshold device which is preset to a predetermined threshold voltage level and incorporates signalling means actuatable when the predetermined threshold voltage level is exceeded by the dc signal.

14. A method according to claim 12 wherein the voltage indicator comprises a voltmeter.

15. A method according to claim 9, wherein said strength of signal developed across said capacitor is indirectly proportional to the dielectric property of the liquid in the bottle.

* * * * *